US011559500B2

(12) United States Patent
Kew

(10) Patent No.: US 11,559,500 B2
(45) Date of Patent: Jan. 24, 2023

(54) COMPOSITIONS AND FORMULATIONS FOR TREATMENT OF MALIGNANCIES

(71) Applicant: Neugate Pharma, LLC, Houston, TX (US)

(72) Inventor: Yvonne Kew, Houston, TX (US)

(73) Assignee: NEUGATE PHARMA, LLC, Houston, TX (US)

( * ) Notice: Subject to any disclaimer, the term of this patent is extended or adjusted under 35 U.S.C. 154(b) by 0 days.

(21) Appl. No.: 16/911,235

(22) Filed: Jun. 24, 2020

(65) Prior Publication Data

US 2020/0330398 A1    Oct. 22, 2020

Related U.S. Application Data

(63) Continuation of application No. PCT/US2018/067754, filed on Dec. 27, 2018.

(60) Provisional application No. 62/611,139, filed on Dec. 28, 2017.

(51) Int. Cl.
| | |
|---|---|
| *A61K 31/07* | (2006.01) |
| *A61K 31/198* | (2006.01) |
| *A61K 31/593* | (2006.01) |
| *A61K 45/06* | (2006.01) |

(52) U.S. Cl.
CPC ............ *A61K 31/07* (2013.01); *A61K 31/198* (2013.01); *A61K 31/593* (2013.01); *A61K 45/06* (2013.01)

(58) Field of Classification Search
CPC .... A61K 31/07; A61K 31/198; A61K 31/593; A61K 45/06
See application file for complete search history.

(56) References Cited

U.S. PATENT DOCUMENTS

2017/0335281 A1* 11/2017 Loew ............. A61K 39/001171

FOREIGN PATENT DOCUMENTS

WO     2017210579 A1    12/2017

OTHER PUBLICATIONS

Roger Stupp, M.D., et al. (Mar. 10, 2005, N Engl J Med 2005; 352:987-996, DOI: 10.1056/NEJMoa043330, Radiotherapy plus Concomitant and Adjuvant Temozolomide for Glioblastoma.*
Burton et al., "A lymphokine, provisionally designated interleukin T and produced by a human adult T-cell leukemia line, stimulates T-cell proliferation and the induction of lymphokine-activated killer cells", Proc. Natd. Acad. Sci. USA vol. 91, pp. 4935-4939, May 1994.
Frei et al., "Histamine receptor 2 modifies dendritic cell responses to microbial ligands", J Allergy Clin Immunol vol. 132, No. 1, Jul. 2013, 23 pages, http://dx.doi.org/10.1016/jjaci.2013.01.013.
Gleissner et al., "Neoplastic meningitis", Lancet Neurol, May 2006, pp. 443-452, vol. 5, http://neurology.thelancet.com.
Gore et al., "Phase I/II Trial of a COX-2 Inhibitor With Limited Field Radiation for Intermediate Prognosis Patients Who Have Locally Advanced Non-Small-Cell Lung Cancer: Radiation Therapy Oncology Group 0213", Original Study, Clinical Lung Cancer, Mar. 2011, pp. 125-130, vol. 12, No. 2, Elsevier Inc., doi: 10.1016/j.cllc.2011.03.007.
Grabstein et al., "Cloning of a T Cell Growth Factor That Interacts with the βChain of the Interleukin-2 Receptor", Science, May 13, 1994, pp. 965-968, vol. 265, No. 5161, American Association for the Advancement of Science, http://www.jstor.org/stable/2883757.
Harstad et al., "Prognostic factors and outcomes in patients with leptomeningeal melanomatosis", Neuro-Oncology, Dec. 2008, pp. 1010-1018.
Iclozan et al., "Therapeutic regulation of myeloid-derived suppressor cells and immune response to cancer vaccine in patients with extensive stage small cell lung cancer", NIH Public Access, Cancer Immunol Immunother, May 2013, vol. 62, No. 5, pp. 909-918, doi:10.1007/s00262-013-1396-8.
Juillerat et al., "Drugs that inhibit gastric acid secretion may alter the course of inflammatory bowel disease", Alimentary Pharmacology and Therapeutics, 2012, pp. 239-247, vol. 36, doi:10.1111/j.1365-2036 2012.05173.x.
Kennedy et al., "Reversible Defects in Natural Killer and Memory CD8 T Cell Lineages in Interleukin 15-deficient Mice", J. Exp. Med., The Rockefeller University Press, Mar. 6, 2000, pp. 771-780, vol. 191, No. 5, http://www.jem.org/cgi/current/full/191/5/771.
Kishimoto, "INTERLEUKIN-6: From Basic Science to Medicine—40 Years in Immunology", Annu. Rev. Immunol, 2005, pp. 1-21, vol. 23, doi: 10.1146/annurev.immunol.23.021704.115806.
Lodolce et al., "IL-15 Receptor Maintains Lymphoid Homeostasis by Supporting Lymphocyte Homing and Proliferation", Immunity, Nov. 1998, pp. 669-676, vol. 9.
MacDonald et al., "Response Criteria for Phase II Studies of Supratentorial Malignant Glioma", Journal of Clinical Oncology, Jul. 1990, pp. 1277-1280, vol. 8, No. 7.
Matsumoto et al., "Cimetidine increases survival of colorectal cancer patients with high levels of sialyl Lewis-X and sialyl Lewis-A epitope expression on tumour cells", British Journal of Cancer, 2002, pp. 161-167, vol. 86, www.bjcancer.com.
O'Mahony et al., "Regulation of the immune response and inflammation by histamine and histamine receptors", Mechanisms of allergic diseases, J. Allergy Clin Immunol, Dec. 2011, pp. 1153-1162, vol. 128, No. 6.
Postow et al., "Immunologic Correlates of the Abscopal Effect in a Patient with Melanoma", The New England Journal of Medicine, Mar. 8, 2012, pp. 925-931, vol. 366, No. 10.

(Continued)

*Primary Examiner* — Barbara P Badio
(74) *Attorney, Agent, or Firm* — Naira Simmons; FisherBroyles, LLP

(57) ABSTRACT

The invention provides compositions, formulations, and methods for treatment of malignancies via activation of an inflammatory response in the subject. Such compositions, formulations, and methods for are preferably used in conjunction with other therapies for the treatment and/or management of malignancies, e.g., chemotherapy and/or radiation. The invention also provides methods of monitoring immune activation in subjects with malignancies.

9 Claims, 11 Drawing Sheets

(56) References Cited

OTHER PUBLICATIONS

Raber et al., "Metabolism of L-Arginine by Myeloid-Derived Suppressor Cells in Cancer: Mechanisms of T cell suppression and Therapeutic Perspectives", NIH Public Access, Immunol Invest., 2012, pp. 614-634, vol. 41(6-7), doi:10.3109/08820139.2012.680634.
Raimondi et al., "Review and meta-analysis on vitamin D receptor polymorphisms and cancer risk", Carcinogenesis, 2009 pp. 1170-1180, vol. 30, No. 7, doi:10.1093/carcin/bgp103.
Sabisz et al., "Modulation of Cellular Response to Anticancer Treatment by Caffeine: Inhibition of Cell Cycle Checkpoints, DNA Repair and More", Current Pharmaceutical Biotechnology, 2008, pp. 325-336, vol. 9.
Scheller et al., "Interleukin-6: From basic biology to selective blockade ofpro-inflammatory activities", Seminars in Immunology, 2013, 11 pages, http://dx.doi.org/10.1016/j.smim.2013.11.002.
Stupp et al., "Radiotherapy plus Concomitant and Adjuvant Temozolomide for Glioblastoma", The New England Journal of Medicine, Mar. 10, 2005, pp. 987-996.
Young et al., "Determining the optimal dosage regimen for H2-recepfor antagonist therapy—a dose validation approach", Aliment. Pkarmacol. Therap. 1989, pp. 47-57, vol. 3.
Inspire, "18 Months In And No Recurrence Yet Of GBM IV" American Brain Tumor Association, Dec. 28, 2016, pp. 1-12, [online] [retrieved on Feb. 19, 2019], Retrieved from internet: <URL: https://www.inspire.com/groups/american-brain-tumor-association/discussion/18-months-in-andno-recurrence-yet/?page=1#replies>; p. 2, post on Dec. 28, 2016 at 8:03am; pp. 5-6, post on Dec. 29, 2016 at 8:30am.
Kochenderfer, J. et al., "Lymphoma Remissions Caused By Anti-CD.1.9 Chimeric Antigen Receptor T Cells Are Associated With High Serum Interleukin-15 Levels", Journal of Clinical Oncology, Jun. 1, 2017, pp. 1803-1813, vol. 35, doi:10.1200/JC0.2016.71.3024; abstract; p. 1810, first column second-third paragraphs; p. 1811, first column second paragraph-second column first paragraph; p. 1812, first column second paragraph.
Long, K. et al., "IL6 Receptor Blockage Enhances Chemotherapy Efficacy in Pancreatic Ductal Adenocarcinoma", Molecular Cancer Therapeutics, Jun. 13, 2017, pp. 1898-1908, vol. 16, No. 9, dol:10.1158/1535-7163.MCT-16-0899; abstract; p. 1899, first column, second paragraph; p. 1899, first column, fourth paragraph; p. 1899, second column, third paragraph; p. 1901, first column, first paragraph-second column, first paragraph; p. 1902, first column, first paragraph; p. 1903, first column, first paragraph; p. 1904, first column, first paragraph-second column, first paragraph; p. 1905, second column, first paragraph.
Shan, Y. et al., "Role of IL-6 in the Invasiveness and Prognosis of Glioma", International journal of Clinical and Experimental Medicine, Jun. 15, 2015, pp. 9114-9120, vol. 8, No. 6, abstract; p. 9114, first column, first paragraph-second column, first paragraph; p. 9115, second column, second paragraph; p. 9118, first column, first paragraph-second column, first paragraph.
PCT/US2018/067754 International Search Report and Written Opinion, dated Mar. 22, 2019.

* cited by examiner

COMPOSITIONS AND FORMULATIONS FOR TREATMENT OF MALIGNANCIES

CROSS-REFERENCE

The present application is a continuation of International Patent Application No. PCT/US2018/067754, filed Dec. 27, 2018, which claims priority to U.S. Provisional Application Ser. No. 62/611,139, filed Dec. 28, 2017, the contents of which are hereby incorporated by reference in their entirety.

FIELD OF THE INVENTION

The present invention relates generally to the fields of oncology and tumor biology.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Malignant cells are normally targeted for elimination by the immune system because of molecular markers that allow the cells to be identified and eliminated by the immune surveillance system. The ability of malignant cells to generate immunosuppression is fundamental to development of advanced stages of many malignancies. In fact, evading tumor elimination from cytotoxic immune cells is essential for development of malignant tumors and subsequent metastasis. Local and systemic immunosuppression tolerates the growth and spread of lethal cancer cells.

Clinical studies suggest that chronic inflammation predisposes individuals to various types of cancers. See, e.g., Balkwill F and Mantovani A (2001) *Lancet* 357(9255): 539-45; Landskron G et al. (2014) *J Immunol Res* 2014: 149185. Chronic inflammation can act locally or distantly through soluble factors including histamine, adenosine, prostanoids and interleukins (IL), which have important roles in the development of host immunosuppression by malignant cells.

Clinical management of malignancies remains an area of significant unmet clinical need. The therapies currently used for various disorders, including conventional chemotherapeutic and/or radiation therapy regimes, often are not successful due to the immunosuppression associated with the tumor. Thus, there remains a pressing need for improved and effective treatments of modulating the immune system in a subject with a malignancy to improve the clinical outcome of various combination therapies, and ways to monitor immune activity in a subject. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The invention provides methods of modulating immune function in a subject having or suspected of having a malignancy. The inflammatory response achieved using the methods and compositions of the disclosure, which includes a change in the ratio of expression and/or activity of particular cytokines, results in a more effective therapeutic outcome in subjects receiving therapy for the malignancy. Such methods are thus preferably used in conjunction with other therapies for the treatment and/or management of malignancies, e.g., chemotherapy and/or radiation.

The invention also provides methods of monitoring immune system competence in subjects with malignancies. Detecting levels of specific immune markers can allow a medical provider to identify subjects with a higher likelihood of successful therapeutic intervention using therapies such as chemotherapy and/or radiation.

In one aspect, the invention provides a method for potentiating chemotherapy and/or radiation therapy in a subject with a malignancy, the method comprising administering a pharmaceutically acceptable dosage of a composition that modulates the subject's immune system, wherein the modulation results in an increase in the expression and/or activity of specific cytokines in a subject. Increasing the ratio of interleukin-15 (IL-15) and interleukin-6 (IL-6) activity and/or expression in a subject, as evidenced by a measured increase of this ratio detected in a sample from a subject receiving the composition. The inflammatory response in the subject is potentiated through the use of an immune modulating regimen that specifically improves the ability of the body to recognize and eliminate tumor cells during the treatment process. The administration of the pharmaceutical composition thus results in an improved clinical outcome in the subject; e.g., an improved response to one or more therapeutic interventions for a malignancy.

Thus, in specific embodiments, the immune modulating regimen comprises administration of a pharmaceutical composition to a subject to decrease levels of IL-6 and/or increase levels of IL-15 as an adjunct to chemotherapy and/or radiation therapy. Such an immune modulating composition can increase a subject's response to tumor therapy as determined by a change in the levels of one or both of these cytokines from about 5% to about 20%, from about 20% to about 45%, from about 45% to about 65% or more. In certain instances, a desired immune response is evidenced by a ratio of IL-15/IL-6 expression and/or activity of 1 or more in the sample from the subject following administration of the pharmaceutical composition.

In another specific embodiment, an immune modulating regime comprises the administration of two or more different compositions that work synergistically to modulate cytokine activity in the immune system of the subject receiving the immune modulating regime. The immune modulating regime preferably increases the ratio of IL-15/IL-6 activity and/or expression to a ratio of one or more in a sample from the subject following administration of the immune modulating regimen.

Following administration of the immune modulating regimen of the disclosure, the increase or decrease in cytokine expression and/or activity can be measured using various different samples from a subject. In some embodiments of the disclosure, the sample tested from the subject is cerebrospinal fluid (CSF). In other embodiments, the sample tested from the subject is another bodily fluid, e.g., blood, plasma or serum.

In one embodiment, the immune modulating regimen of the present invention is used in conjunction with chemotherapeutics, alone or in conjunction with radiation. In other embodiments, the present invention is use with radiation alone.

In a specific embodiment, the immune modulating regime is a composition and/or formulation that comprises at least three essential components: a histamine H2 receptor antagonist; an adenosine 2A receptor inhibitors; and a nonsteroidal anti-inflammatory drug (NSAID), e.g., a cox-2 inhibitor. Certain compositions contain a single compound from each of the three classes. Other aspects may contain a combination of one or more of components in each class, e.g., two or more NSAIDs or histamine H2 receptor antagonists. Preferably, the methods of the disclosure further utilized vitamin A, a vitamin D receptor ligand, and/or citrulline.

The invention thus provides administration of pharmaceutical compositions for modulating the immune system of a subject with a malignancy, the composition comprising a histamine H2 receptor antagonist, an adenosine 2A receptor inhibitor, and an NSAID that inhibits COX-2. In certain embodiments, the composition further vitamin A, a vitamin D receptor ligand (e.g., cholecalciferol) and/or citrulline. The desired immune modulation is evidenced by an increase in the ratio of IL-15/IL-6 expression and/or activity in a sample from the subject. In some aspects, the components of the composition and/or formulation are administered together. In other aspects, at least two components of the formulation are administered separately.

In some embodiments, the invention provides a method for predicting the likelihood a subject will respond to a therapeutic intervention for a malignancy, and administering therapeutic intervention if the subject displays a favorable cytokine ratio. This method comprises requesting a test to determine the ratio of IL-15/IL-6 expression and/or activity in a sample from the subject and administering therapeutic intervention to the subject if the ratio of IL-15/IL-6 expression and/or activity in the sample from the subject is one or greater.

The therapeutic interventions that may be used in conjunction with the immune modulating regimen of the disclosure include, but are not limited to, chemotherapy, radiation, surgery, immunotherapy, targeted therapy, hormone therapy and stem cell therapy. In a preferred embodiment, therapeutic intervention is chemotherapy. In other embodiments, therapeutic intervention is radiation. In yet other embodiments, therapeutic intervention is both chemotherapy and radiation.

The subject's response to the immune modulating regimen can be tested to identify an increase in the ratio of IL-15/IL-6 expression and/or activity in the subject any time after the immune modulating regimen is administered to the subject. In some embodiments, the composition is administered at least 1-2 days before testing the subject to identify an increase in the ratio of IL-15/IL-6 expression and/or activity. In other embodiments, the composition is administered at least 5 days before testing the subject. In yet other embodiments, the composition is administered at least 10 days before testing the subject to identify an increase in the ratio of IL-15/IL-6 expression and/or activity. The ratio of IL-15/IL-6 expression and/or activity may also be monitored in the subject throughout treatment for the malignancy to ensure the levels remain at a desired level to provide an improved clinical outcome.

The immune modulating regimen administered to the subject prior to testing for the ratio of IL-15/IL-6 expression and/or activity preferably comprises a histamine H2 receptor antagonist, an adenosine 2A receptor inhibitor, and an NSAID that inhibits COX-2. In some embodiments, the composition further comprises vitamin A. In other embodiments, the composition further comprises a vitamin D receptor ligand; e.g., cholecalciferol. In still other embodiments composition further comprises citrulline. In a preferred embodiment, the composition comprises a histamine H2 receptor antagonist, an adenosine 2A receptor inhibitor, an NSAID that inhibits COX-2, vitamin A, vitamin D receptor ligand, and citrulline.

In other embodiments, the invention provides a method of treating a malignancy, the method comprising: administering to a subject a composition that increases the IL-15 expression levels in a sample from the subject, wherein the increase in IL-15 is associated with an increase in the antibody-dependent cellular cytotoxicity (ADCC) of natural killer (NK cells), such that the increase in ADCC of the NK cells results in an improved response to one or more therapeutic interventions for the malignancy.

In yet other embodiments, the invention provides a method of treating a malignancy, the method comprising: administering to a subject a composition that increases the IL-15 expression levels in a sample from the subject, wherein the increase in IL-15 is associated with an increase in the CTL (cytotoxic T lymphocyte) activity, such that the increase in CTL activity results in an improved response to one or more adjunct therapeutic interventions for the malignancy.

The invention further provides a method of treating a malignancy, the method comprising: administering to a subject a composition that decreases the IL-6 expression levels in a sample from the subject, wherein the decrease in IL-6 is associated with a decrease in tumor autoimmunity in the subject, and wherein the decrease in IL-6 results in an improved response to one or more adjunct therapeutic interventions for the malignancy.

These aspects and other features and advantages of the disclosure are described below in more detail. Those skilled in the art will recognize, or be able to ascertain using no more than routine experimentation, many equivalents to the specific embodiments of the disclosure described herein. Such equivalents are intended to be encompassed by the following claims.

DEFINITIONS

Figure 1:
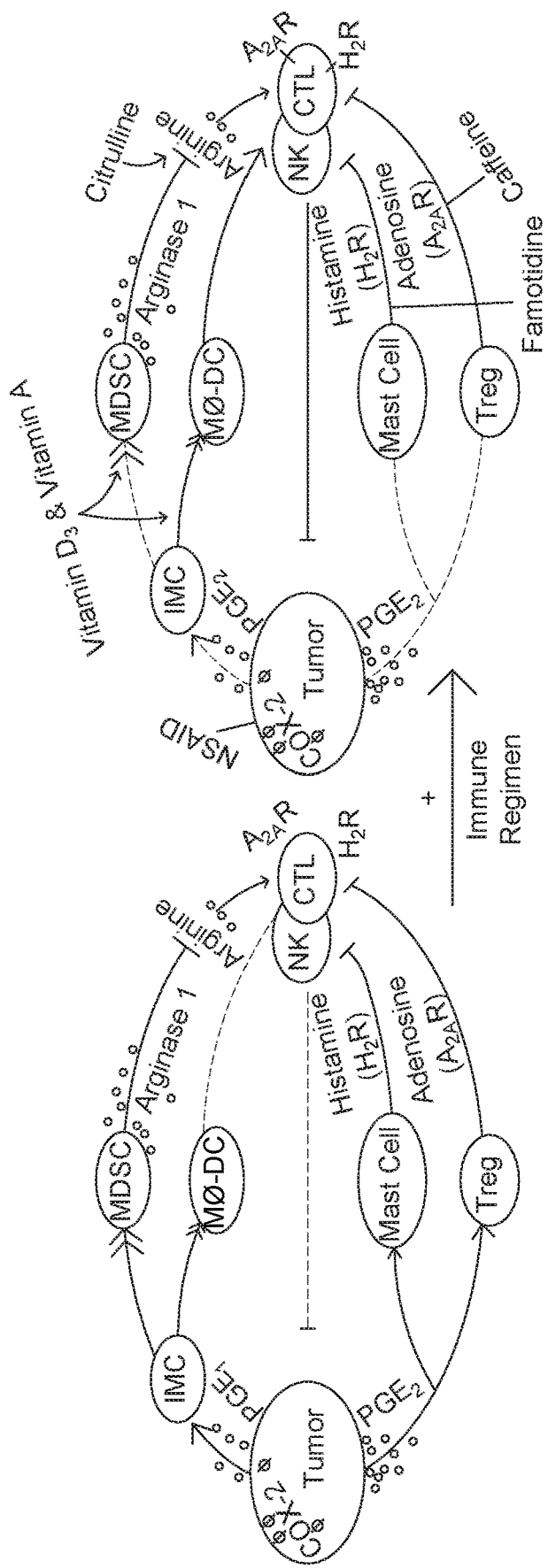
FIG. 1 is a diagram illustrating immune modulatory mechanisms of components of the compositions and formulations of the disclosure.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The terms "malignancy", "cancer" and variations thereof include solid and hematological tumors, and the present invention contemplates treating them both. "Solid tumors" are exemplified by tumors of the breast, bladder, bone, brain, central and peripheral nervous system, cervix, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, sarcoma, skin (e.g., melanoma), small intestine, stomach (or gastric cancer), soft tissue, testis, ureter, vagina and vulva. Malignant neoplasias include inherited cancers exemplified by Retinoblastoma and Wilms tumor. In addition, malignant neoplasia include primary tumors in said organs and corresponding secondary tumors in distant organs ("tumor metastases"). Hematological tumors are exemplified by leukemia and lymphoma, namely non-Hodgkins disease, chronic myeloid leukemia (CML), acute myeloid leukemia (AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as viral-related malignancies (e.g., Kaposi's sarcoma and cervical cancer).

The term "excipient" as used herein refers to a compound that is useful in preparing a pharmaceutical composition, generally safe, non-toxic and neither biologically nor otherwise undesirable. The compositions of this invention can be administered alone but will generally be administered in admixture with one or more suitable pharmaceutical excipients, diluents or carriers selected with regard to the intended route of administration and standard pharmaceutical practice.

The term "pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "composition" as used herein can refer to ingredients within a single dosage form or a within a combination of dosage forms that are administered to the subject simultaneously or sequentially.

DETAILED DESCRIPTION OF THE DISCLOSURE

The practice of the methods and compositions described herein may employ, unless otherwise indicated, conventional techniques of pharmaceutical chemistry, drug formulation techniques, dosage regimes, and biochemistry, all of which are within the skill of those who practice in the art. Such conventional techniques include the use of combinations of therapeutic regimes including but not limited to the methods described herein; technologies for formulations of adjunct therapies used in combination with known, conventional therapies and/or new therapies for the treatment of various malignancies, delivery methods that are useful for the compositions of the disclosure, and the like. Specific illustrations of suitable techniques can be had by reference to the examples herein.

Such conventional techniques and descriptions can be found in standard laboratory and physician manuals, as will be apparent to those skilled in the art upon reading the present disclosure.

Note that as used herein and in the appended claims, the singular forms "a," "an," and "the" include plural referents unless the context clearly dictates otherwise. Thus, for example, reference to "a composition" refers to one or more compositions, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

The present invention provides methods, including useful compositions and formulation for use in such, for potentiating therapeutic intervention (e.g., chemotherapy and/or radiotherapy) in subjects with malignancies. The invention was based on the surprising finding that altering the ratio of IL-15/IL-6 expression and/or activity via modulation of the subject's immune system had a significant effect on the course of the subject's response to chemotherapy and/or radiation. In particular, the present invention was based on the novel finding that increased IL-15 levels were associated with reproducible, robust radiological responses with abscopal effects that corroborate amelioration of immune suppression.

Reversal of tumor immunosuppression was accomplished by administration of the immune modulating regimen in addition to chemoradiotherapy ("CRT"). Providing subjects with a composition to return them a relatively "immunocompetent state" allows the immune system of the subject to aid in therapeutic intervention by fostering increased elimination of remaining intact tumor cells via the subject's immune system. The ratio of IL-15/IL-6 expression and/or activity in CSF and other body fluids is a potential marker for tumor response when immune therapy is instituted. Prospective clinical trials are needed to validate our findings. Furthermore, our observed clinical responses propose a paradigm shift whereby future therapeutic interventions could including strategies to reverse tumor immunosuppression as well as targeting direct killing of the tumor cells.

An increase in the ratio of IL-15/IL-6 expression and/or activity of multiple subjects was achieved using an immune modulating regimen that increased a subject's immune response and allowed the subjects to have an improved response to chemoradiotherapy. The immune modulating regimen included three primary components: histamine H2 receptor antagonist, an adenosine 2A receptor inhibitor, and an NSAID that inhibits COX-2. The specific regime used for a proof of concept included the three primary components as well as vitamin A, cholecalciferol, and citrulline. For ease of discussion herein, the particular combination of components is referred to as the immune modulating regimen.

The clinical features possessed by subjects that best predicted clinical and/or radiographic response to the immune modulating regimen were subjects newly diagnosed compared to recurrent disease, and those with cancerous meningitis ("ventriculitis") compared with parenchymal tumor. The unique microenvironment of leptomeninges and ventricles, compared to solid parenchymal tumor, more readily allows immune reactivation once the appropriate balance has been restored. Newly diagnosed tumors may be more responsive because they are less likely to have leukocytopenia from prior chemotherapy and less likely to be molecularly heterogenous than recurrent disease, thus, more easily targeted by a reactivated immune system.

The specific actions of each agent of the exemplary immune modulating regimen used in one aspect of the disclosure are described in FIG. 1. As illustrated in FIG. 1, tumor cells impose an immune privileged microenvironment through recruitment of immunosuppressive cells and secretion of inhibitory factors that act to suppress immune activities against tumor cells (panel A, left side). On the right side, are locations where components of the immune modulating regimen block and/or reverse tumoral immune-repressive mechanisms. Caffeine and famotidine block $A_{2A}$ (adenosine$_{2A}$) and $H_2$ (histamines) receptors, respectively, on effector CTLs and NKs. Celecoxib inhibits production of prostaglandin $E_2$ (PGE$_2$) by cyclooxygenase 2 (COX-2) expressed by tumor cells and MDSCs. Cholecalciferol (vitamin $D_3$) and vitamin A promote differentiation of myeloid cells and macrophage differentiation away from immature suppressive states, such as immature MDSC. Finally, the L-arginine metabolic precursor, L-citrulline, was used to restore intracellular L-arginine levels within cytotoxic cells to allow recovery of T cell and natural killer (NK) cell function.

Compositions for Modulation of Cytokine Expression and/or Activity

The ability of neoplastic cells to generate immunosuppression is fundamental to development of many malignancies. Local and systemic immunosuppression leads to the tolerance towards the growth and metastasis of tumor cells. Tumor cells impose an immune privileged microenvironment through recruitment of immunosuppressive cells and secretion of inhibitory factors that act to suppress immune activities against tumor cells.

Cytokines such as interleukin-16 (IL-6) promote activation of immunosuppressive myeloid cells (myeloid-derived suppressor cells [MDSC]) and, thereby, the proliferation and survival of malignant cells (Kishimoto T, *Annu Rev Immunol* (2005) 23: 1-21. Additionally, IL-6 is a key promoter of angiogenesis, neoplastic invasion and metastasis. Elevated IL-6 levels have been implicated in different stages of tumor development and spread, especially in advanced metastatic cancers (Scheller J et al., *Semin Immunol* (2014) 26(1): 2-12).

In contrast to the pro-tumorigenic functions of IL-6, IL-15 is an inflammatory cytokine, which stimulates innate and adaptive immune cell activation and is critical in facilitating tumor destruction. Lodolce J P et al. *Immunity* (1998) 9(5): 669-76; Kennedy M K, et al. *J Exp Med* (2000) 191(5): 771-80; Burton J D et al. *Proc Natl Acad Sci USA* (1994) 91(11): 4935-9; Grabstein K H et al. *Science* (1994) 264 (5161): 965-8. IL-15 induces maturation and activation of dendritic cells, enhances proliferation, development and activation of immune effector cells such as natural killer cells (NK) and cytotoxic T lymphocytes (CTL), and sustains memory T cells.

Both adaptive and innate immune cells participate in the surveillance and the elimination of tumor cells. One primary adaptive cell type is cytotoxic T lymphocytes (CTL). Among the innate cells are natural killer cells (NK cells), which constitute a major component of the innate immune system. NK cells play a major role in the rejection of tumors and cells infected by viruses. The cells kill by releasing small cytoplasmic granules of proteins called perforin and granzyme that cause the target cell to die by apoptosis. In specific methods of the disclosure, the antibody-dependent cellular cytotoxicity (ADCC) of natural killer (NK cells) is specifically augmented, which in turn enhances tumor cell killing.

Conventional cytotoxic chemotherapies induce myelosuppression, decreasing the population of NK cells, thereby reducing the efficacy of ADCC. The compositions of the disclosure which increase IL-15 levels, and thus the IL-15/IL-6 expression ratio, may augment NK cell function through enhancing ADCC, and offer the ability to improve activity of chemotherapy and/or radiation therapy, including monoclonal antibody therapy, without increasing toxicity to non-cancer cells.

ADCC is a primary mechanism by which tumor directed monoclonal antibody therapy works. Increasing the ADCC in a subject undergoing monoclonal antibody therapy may be especially useful, as it may increase the subject's response to the therapy as well as increase the subject's own ability to destroy tumor cells.

By increasing the numerator of the ratio of IL-15/IL-6 expression and/or activity, the methods of the disclosure increase the subject's own ability to recognize and destroy tumor cells and thus enhance the anti-tumor effect of therapies including chemotherapy and/or radiation therapy. Specifically, the methods enhancing IL-15 expression and/or activity may enhance the ability of the subject's immune system to respond to one or more tumor antigen(s).

Accordingly in some embodiments, the present invention provides a method to increase the IL-15 6 activity and/or expression in a subject receiving treatment for a malignancy by administering a composition that increases IL-15 activity in the subject, e.g., prior to administration of a therapeutic intervention or for a period of time during the therapeutic intervention. Preferably, the composition that increases IL-15/IL-6 activity and/or expression in the subject is administered for the duration of the treatment the subject is receiving for a particular malignancy.

In one embodiment, the ADCC function in a subject is augmented and tumor cell killing is enhanced by sequential or simultaneous administration of a conventional therapy an immune modulating therapy that increases IL-15 activity and ADCC function. In another embodiment, the CTL activity in a subject is augmented and tumor cell killing is enhanced by sequential or simultaneous administration of a conventional therapy an immune modulating therapy that increases IL-15 activity and ADCC function. Preferably, the increase in IL-15 activity is associated with both an increase in ADCC function and CTL activity.

The IL-15 agonists for use in the methods of the present invention include any molecule (natural or synthetic) that activate or enhance signal transduction by IL-15 and promote the biological activity of IL-15. Specific examples of IL-15 agonists include molecules that bind to IL-15, molecules that increase IL-15 expression, molecules that bind to an IL-15 receptor, and molecules that increase the expression of an IL-15 receptor, including but not limited to, an antibody or fragments thereof, small molecules, peptides or partial peptides of IL-15 or IL-15 receptor, proteins (including derivative proteins), aptamers, and soluble IL-15 receptors. Such agonists for use with the methods of the disclosure to increase IL-15 activity are disclosed in references including, but are not limited to, U.S. App. No. 20140205560, U.S. App. No. 20130336924, U.S. App. No. 20120230946, U.S. App. No. 20110158938, and U.S. App. No. 20090324538.

Another approach envisioned in the methods of the present invention is administration of an immune modulating regime that comprises an IL-6 antagonist. By decreasing the denominator of the ratio of IL-15/IL-6 expression and/or activity, the methods of the invention decrease immunosuppression protecting the tumor cells from destruction by the subject's immune system and thus enhance the anti-tumor effect of therapies including chemotherapy and/or radiation therapy. Specifically, the methods reducing IL-6 expression and/or activity may enhance the ability of the subject's immune system to respond to one or more tumor antigen(s).

Accordingly in some embodiments, the present invention provides a method to decrease the IL-6 expression and/or activity in a subject receiving treatment for a malignancy by administering a composition that decreases IL-6 activity and/or expression in the subject, e.g., prior to administration of a therapeutic intervention or for a period of time during the therapeutic intervention. Preferably, the composition that decreases IL-6 activity and/or expression in the subject is administered for the duration of the treatment the subject is receiving for a particular malignancy.

The IL-6 antagonists for use in the methods of the present invention include any molecule (natural or synthetic) that blocks signal transduction by IL-6 and inhibit the biological activity of IL-6. Specific examples of IL-6 antagonists include molecules that bind to IL-6, molecules that inhibit IL-6 expression, molecules that bind to an IL-6 receptor, and molecules that inhibit the expression of an IL-6 receptor, including but not limited to, an antibody or fragments thereof, small molecules, peptides or partial peptides of IL-6 or IL-6 receptor, proteins (including derivatized proteins), aptamers, soluble IL-6 receptors, and antisense or siRNAs directed to IL-6 or IL-6R. Such antagonists for use with the methods of the disclosure to decrease IL-6 activity are disclosed in references including, but are not limited to, tocilizumab, atlizumab, and those molecules described in U.S. App. No. 20150337036, U.S. App. No. 20150191540, U.S. App. No. 20130336924 U.S. App. No. 20130323238, U.S. App. No. 20130101598, U.S. App. No. 20130028860, U.S. App. No. 20120128626, U.S. App. No. 20110038877, U.S. App. No. 20100150829, U.S. App. No. 20100129357, U.S. App. No. 20070178098, U.S. App. No. 20050090453, and U.S. App. No. 20030186876.

Histamine Antagonists

The microbiota is important for optimal host development and for ongoing immune homeostasis. The composition and metabolic activity of the microbiota has profound effects on mucosal tolerance and pathological responses. The innate immune response depends on the recognition of microbe-associated molecular patterns by pattern recognition receptors on host cells, such as dendritic cells (DCs). The induction of tolerance and protective immunity to microbes is significantly influenced by host- and microbiota-derived metabolites, such as histamine. Differential binding of microbe-associated molecular patterns to receptors leads to a complex array of interconnecting intracellular signaling pathways, which influence cellular metabolism, cytokine and chemokine secretion, antigen presentation, and cell-surface costimulatory and inhibitory molecule expression.

For example, histamine is believed to exert immunoregulatory effects via the activation of 4 different histamine receptors. O'Mahony L, Akdis M, Akdis C A. J Allergy Clin Immunol 2011; 128: 1153-62. Activation of histamine receptor 2 (H2R) is associated with potent immunoregulatory effects. The anti-inflammatory effects of a histamine secreting L rhamnosus strain were lost in H2 receptor-deficient animals, suggesting that histamine derived from the microbiota may be immunoregulatory. Frei R, et al. J Allergy Clin Immunol 2013; 132:194-204. In addition, histamine has been demonstrated to modulate toll-like receptor-induced cytokine secretion from human dendritic cells. The physiological effect of this immunomodulation in subjects with different disorders is not clear, however, as pro-inflammatory responses to nonpathogenic challenge could be considered protective, whereas excessive suppression of the inflammatory response to infectious agents or cancer cells might be detrimental, resulting in immune evasion and pathogen persistence.

More recently, the activity of H2 receptor antagonists has been associated with changes in the immune response in human subjects with different disorders. For example, in subjects with inflammatory bowel disease, the administration of an H2 receptor antagonist was associated with an alteration in the pathophysiology of the disease. Juillerat P et al, Aliment Pharmacol Ther. (2012) August; 36(3):239-47. Again, given the uncertainty of the effects of immunoregulation via histamine modulation, it was unclear prior to the present invention that compositions and formulations containing H2 receptor antagonists would accelerate and/or potentiate conventional chemotherapeutic and/or radiation therapies for malignancies. Without being bound to a theory, the suppression of H2 receptor activity bolsters a subject's immune system, having the effect of not only improving the subject's response to pathogens but also allowing cells of the immune system (e.g., natural killer or "NK" cells) to better recognize and eliminate malignant cells.

$H_2$ receptor antagonists are a class of drugs that block the action of histamine through the histamine $H_2$ receptors. The conventional $H_2$ antagonists are competitive antagonists of histamine, e.g., at the parietal cell $H_2$ receptor. They suppress the normal secretion of acid by parietal cells and the meal-stimulated secretion of acid. They accomplish this by two mechanisms: Histamine released by ECL cells in the stomach is blocked from binding on parietal cell $H_2$ receptors, which stimulate acid secretion; therefore, other substances that promote acid secretion (such as gastrin and acetylcholine) have a reduced effect on parietal cells when the $H_2$ receptors are blocked. Certain $H_2$-agonists function as inverse agonists rather than receptor antagonists, due to the constitutive activity of these receptors.

$H_2$ receptor antagonists for use in the present invention include, but are not limited to, ranitidine (Zantac®), cimetidine (Tagamet®) nizatidine (Axid®) and famotidine (Pepcid). The dosage of $H_2$ receptor antagonists for use in the invention can be determined based on knowledge of the particular $H_2$ receptor antagonist used, the other treatments and medications a subject may be receiving, and other the needs of the subject(s) as will be known by those of ordinary skill in the art.

The appropriate dosage of H2 receptor antagonists can be determined using methods known to those of ordinary skill in the art (See, e.g., Young M D et al., Alimentary Pharmacology & Therapeutics (1989) 3:1, 47-57.

Non-Steroidal Anti-Inflammatory Drugs

The third essential component of the compositions and/or formulations of the disclosure is one or more non-steroidal anti-inflammatory drugs (NSAIDs) that act by blocking the production of prostaglandins that cause inflammation and pain, cyclooxygenase-1 (COX-1) and/or cyclooxygenase-2 (COX-2). Traditional NSAIDs work by blocking both COX-1 and COX-2. The COX-2 selective inhibitors block only the COX-2 enzyme.

Traditional NSAIDs for use in the invention include, but are not limited to, aspirin, indomethacin (Indocin®), ibuprofen (Advil®, Motrin®), naproxen (Naprosyn®), piroxicam (Feldene®), and nabumetone (Relafen®). Preferably, NSAIDs for use in the invention are COX-2 selective inhibitors. Blocking the COX-2 enzyme, while allowing the COX-1 enzyme to work decreases the chance of having a stomach ulcer and/or bleeding. Such COX-2 selective inhibitors include, but are not limited to, celecoxib)(Celebrex®, rofecoxib)(Vioxx®, and valdecoxib (Bextra).

The dosage of the NSAID for use in the invention can be determined based on knowledge of the particular NSAID used, the other treatments and medications a subject may be receiving, and other the needs of the subject(s) as will be known by those of ordinary skill in the art. For example, celecoxib (Celebrex) is conventionally prescribed in 100 mg or 200 mg capsules and the general dose (e.g., for pain caused by arthritis) is generally between 100-400 mg a day.

Formulations

The compositions of the present invention may be formulated in a wide variety of oral administration dosage forms and carriers. Oral administration can be in the form of tablets, coated tablets, dragees, hard and soft gelatin capsules, solutions, emulsions, syrups, or suspensions. Compositions of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the subject's response to the active ingredient.

Compositions of the present invention, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active components, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of sterile injectable solutions for parenteral use. A typical preparation will contain from about 5% to about 95% active compositions (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compositions of the present invention may be formulated for parenteral administration (e.g., by injection, for example bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile free water.

When desired, formulations can be prepared with enteric coatings adapted for sustained or controlled release administration of the active ingredient. For example, the Compositions of the present invention can be formulated in transdermal or subcutaneous drug delivery devices. These delivery systems are advantageous when sustained release of the compound is necessary and when subject compliance with a treatment regimen is crucial. Compositions in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modifications of the present compositions to modify the route of administration and dosage regimen of a particular compound in order to manage the pharmacokinetics of the present compositions for maximum beneficial effect in subjects are well within the ordinary skill of the art.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the subject, other medicaments with which the subject is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual subject is reached. One of ordinary skill in treating diseases described herein will be able, without undue experimentation and in reliance on personal knowledge, experience and the disclosures of this application, to ascertain a therapeutically effective amount of the Compositions of the present invention for a given disease and subject.

In preferred aspects, the composition is administered orally. For example, the immune modulating regimen is preferably an oral regimen, which includes famotidine 40 mg twice a day; vitamin A 10,000 IU daily; caffeine 200-400 mg daily; celecoxib 200 mg twice a day; citrulline 3 gm twice a day; cholecalciferol (vitamin $D_3$) 5,000 IU twice a day.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Combination Therapies

In some embodiments, the present invention contemplates using the immune modulating compositions of the disclosure in "combination therapy" or as "adjunct therapy." As used herein, these terms are used to indicate that the compositions can be used before, after or together with some other type of therapy or therapies, including but not limited to surgery, radiation, and chemotherapy. Examples of known chemotherapeutic anti-cancer agents frequently used for combination therapy include, but not are limited to (i) alkylating/carbamylating agents such as Cyclophosphamid, Ifosfamid, Thiotepa, Melphalan, or chloroethylnitrosourea (BCNU); (ii) platinum derivatives like cis-platin, oxaliplatin or carboplatin; (iii) antimitotic agents/tubulin inhibitors such as vinca alkaloids (vincristine, vinblastine, vinorelbine), taxanes such as Taxol, Taxotere and analogs as well as new formulations and conjugates thereof; (iv) topoisomerase inhibitors such as anthracyclines such as Doxorubicin, epipodophyllo-toxines (such as Etoposide) and camptothecin analogs such as Topotecan; (v) pyrimidine antagonists such as 5-fluorouracil (5-FU), Capecitabine, Arabinosylcytosine/Cytarabin or Gemcitabine; (vi) purin antagonists such as 6-mercaptopurine, 6-thioguanine or fludarabine, and (vii) folic acid antagonists such as methotrexate and pemetrexed.

Other classes of agents contemplates in the context of combination therapy include but are not limited to (i) kinase inhibitors such as e.g. Gleevec, ZD-1839/Iressa, Bay43-9006, SU11248 or OSI-774/Tarceva; (ii) proteasome inhibitors such as PS-341; (iii) histone deacetylase inhibitors like SAHA, PXD101, MS275, MGCD0103, Depsipeptide/FK228, NVP-LBH589, Valproic acid (VPA) and butyrates; (iv) heat shock protein inhibitors like 17-allylaminogeldanamycin (17-MG); (v) vascular targeting agents (VAT) and anti-angiogenic drugs like the VEGF antibody Avastin or the KDR tyrosine kinase inhibitor PTK787/ZK222584; (vi) monoclonal antibodies such as Herceptin or MabThera/Rituxan or C225/Erbitux as well as mutants and conjugates of monoclonal antibodies and antibody fragments; (vii) oligonucleotide based therapeutics like G-3139/Genasense; (viii) protease inhibitors (ix) hormonal therapeutics such as anti-estrogens (e.g. Tamoxifen), anti-androgens (e.g. Flutamide or Casodex), LHRH analogs (e.g. Leuprolide, Goserelin or Triptorelin) and aromatase inhibitors.

Still other known anti-cancer agents which can be used for combination therapy include bleomycin, retinoids such as all-trans retinoic acid (ATRA), DNA methyltransferase inhibitors such as the 2-deoxycytidine derivative Decitabine, alanosine, cytokines such as interleukin-2 or interferons such as interferon-gamma, TRAIL, DR4/5 agonistic antibodies, FasL- and TNF-R agonists.

Radiation Sensitizer

Tumor treatment via the use of ionizing radiation can be enhanced by increasing the radiosensitivity of the tumor cells. In one embodiment, the present invention contemplates utilizing the immune modulating compositions of the present invention to enhance radiosensitivity. The ideal radiation sensitizer should reach the tumor in adequate concentrations and have predictable pharmacokinetics for timing with radiation treatment and could be administered with every radiation treatment. The ideal radiation sensitizer should have minimal toxicity itself and minimal or manageable enhancement of radiation toxicity. It is believed that the compositions of the disclosure satisfy these demands since every component of the compositions of the disclosure is safe and non-toxic.

The subject with cancer can be given the composition systemically (e.g. orally or by intravenous administration) or locally (e.g. by intratumoral injection or implant) prior to radiation. It is not intended that the present invention be limited by the particular timing or dosing. In one non-limiting example, the present invention contemplates an embodiment whereby the human or animal is administered a composition of the present invention at relatively low dosage levels (e.g. 0.5 to 50 ug/kg) prior to radiation. Administration the inflammatory compositions described herein together with radiation provides enhanced tumor cell killing and thus an advantage in the treatment of human malignancies. Importantly, the combination therapy may allow a lower dose of irradiation to be used.

Electromagnetic Stimulation

In certain aspects, the compositions and methods of the disclosure are used prior, after, or in conjunction with application of brain stimulation therapies, and in particular application of electromagnetic energy at or near a region of malignancy. In such aspects, the electromagnetic energy is induced by using magnetic fields applied to the head.

In certain specific aspects, transcranial magnetic stimulation (TMS) is used with the compositions and methods of the disclosure, encompassing all forms. TMS is a non-invasive treatment that uses electromagnetic pulses to stimulate neurons. When the device is positioned to targeted areas of the brain, the frequency of these stimulations selectively modifies neuronal connections, which can be used to create positive outcomes in patients. This technique has been FDA approved, e.g., for drug resistant Major Depressive Disorder and is being researched as a promising method for improving post-stroke recovery as well as other psychiatric and neurological disorders. See, e.g., Smith, M C, and C M Stinear. *Current Neurology and Neuroscience Reports*, U.S. National Library of Medicine, September 2016.

Published clinical and pre-clinical studies support TMS' role in neural repair. The TMS created magnetic field pulses interacts with the brain, which is physically functioning as a conductor, to cause neuronal depolarization. This enhances neuronal connections. The frequency of stimulation is important as it determines whether the synaptic communication between neurons are made more efficient, a process known as long term potentiation (LTP), or less efficient, long term depression (LTD). M. Sauvé, et al. (2014). The Science of Transcranial Magnetic Stimulation. Psychiatric Annals. 44. 279-283. The placement of the TMS device and chosen frequency can thus selectively strengthen or weaken synaptic connections in the brain, which may explain some of its long term benefits and clinical utility.

Motor evoked potentials (MEP) are recorded electrical signals from neuronal tissue following activation and are easily detectable manifestations of TMS effects on neurons and their microenvironment. This neuronal motor response is often used in pre-surgical mapping of eloquent brain areas such as language and motor activities.

TMS has also been shown to alter gene expression, suggesting that TMS can positively impact genes known to affect multiple recovery promoting pathways. A study exploring the induction of changes in gene expression after acute ischemic-reperfusion brain injury in rats showed increased expression of 52 genes after two weeks of treatment. The upregulated genes included those involved in inflammation, injury response, cellular repair, structural remodeling, neuroprotection, neurotransmission and neuronal plasticity. Ljubisavljevic M R et al. (2015), PLoS ONE 10(10): e0139892.

In utilizing TMS for neuronal repair and recovery from chemoradiation therapy-related side effects, an unexpected regression in tumor size was also observed when TMS was given with compositions of the disclosure, in combination with rescue therapy for tumor recurrence (data not shown). Without being bound to a particular mechanism, these improved outcomes could derive from mechanisms related to TMS induced tissue repair, possibly decreasing local IL-6 production.

EXAMPLES

The following examples are put forth so as to provide those of ordinary skill in the art with a complete disclosure and description of how to make and use the present invention, and are not intended to limit the scope of what the inventors regard as their invention, nor are the examples intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1: Proof of Concept with an Exemplary Formulation of the Disclosure

Reversal of cancer immunosuppression using compositions that modulate a subject's immune system, as evidenced by cytokine alterations and clinical responses, was demonstrated despite heterogenous cancer subtypes. Subjects used in the larger study were diagnosed with different primary or metastatic tumors involving the central nervous system: glioblastoma, carcinoma, or lymphoma. The oral immunomodulation regimen was offered to subjects in addition to standard therapy.

The present experiments used specific components to target and interfere with immunosuppression. The exemplary formulation used in the experiments described herein was referred to as the immune modulating regimen, and this formulation was intended to elicit an immune response when given in concert with CRT. Each component has been studied alone, exhibiting only modest effects as single-agent therapy against renal cell, head and neck, colon, or lung cancer. Gore E et al. *Clinical Lung Cancer* (2011) 12(2): 125-30; Iclozan C, et al. *Cancer Immunol Immunother* (2013) 62(5): 909-18; Matsumoto S et al. *Br J Cancer* (2002); 86(2): 161-7; Raber P et al. *Immunol Invest* (2012) 41(6-7): 614-34; Sabisz M and Skladanowski A. *Curr Pharm Biotechnol* (2008); 9(4): 325-36. Raimondi S et al. *Carcinogenesis* (2009) 30(7): 1170-80. The proposed mechanisms of the various components are summarized in Table 1:

TABLE 1

Action and Effects of Components of the immune modulating regimen

| Immune Regimen | Action | Proinflammatory Effects |
|---|---|---|
| Famotidine | Histamine 2 receptor blocker | Reverses CTL inhibition |
| Vitamin A | RXR ligand | Enhances DC and NK cell differentiation and up regulates IFNγ |
| Caffeine | Adenosine Receptor 2 A blocker | Blocks Treg - mediated adenosine suppression of CTLs |
| Meloxicam | Blocks cyclooxygenase 2 selective inhibitor & $PGE_2$ | Blocks MDSC differentiation and activation of Treg and MDSCs |
| Citrulline | Replace L-arginine via urea cycle | Counters MDSC suppression of NKs and CTLs |
| Cholecalciferol | Vitamin D Receptor (VDR) ligand | Promotes myeloid lineage development, up regulates IFNγ |

Thirty-eight subjects with a diagnosis of malignant primary or metastatic tumors involving the CNS, including 24 glioblastoma subjects (GB), 7 with metastatic carcinoma (M), 4 with primary brain tumors (PB), and 3 primary CNS lymphoma were used in the proof of concept study. An immune modulating regimen comprising the components listed in Table 1 was offered to each subject. Samples were collected at scheduled clinic visits. Whole blood samples were collected in polypropylene tubes and stored at 4° C. for 2-3 hours to clot, followed by centrifugation for 10 minutes at 2,000×g at 4° C. to obtain sera. Sera and CSF were stored at −20° C. awaiting cytokine profiling. Along with standard blood or CSF collection, excess sera and CSF were gathered and stored. Radiology studies were performed as part of standard evaluation. Tumor responses were determined by Macdonald criteria (Macdonald D R et al, *J Clin Oncol* (1990) 8(7): 1277-80). A clinical summary of the 38 subjects is shown below in Table 2.

TABLE 2

Clinical Summary of the 38 Subjects in the Immune Modulation Regimen Proof of Concept Study

| Case | Diagnosis | Diagnosis Age | Sex | MGMT | IDH1 | Cancerous Meningitis/ Ventriculitis | Immune Regimen | Response | Abscopal Effect | OS from Dx (weeks) | OS from Recurrence (weeks) | Cause of Death |
|---|---|---|---|---|---|---|---|---|---|---|---|---|
| rM1 | Melanoma | 53 | F | Ummethylated | Wild Type | + | Yes | Near CR | Yes | >56, alive | >36 | Aive |
| nM2 | CUP | 74 | F | ND | ND | + | Yes | CR | Yes | 34 | — | CHF |
| nM3 | NSCLC | 79 | F | ND | ND | + | Yes | CR | Yes | 51 | — | VPS failure |
| nM4 | GE | 60 | M | Ummethylated | Wild Type | + | Yes | CR | Yes | >36, alive | — | Alive |
| rM5 | Breast Cancer | 60 | F | ND | ND | + | Yes | PR | — | >186, alive | >89, alive | Alive |

TABLE 2-continued

Clinical Summary of the 38 Subjects in the Immune Modulation Regimen Proof of Concept Study

| Case | Diagnosis | Diagnosis Age | Sex | MGMT | IDH1 | Cancerous Meningitis/ Ventriculitis | Immune Regimen | Response | Abscopal Effect | OS from Dx (weeks) | OS from Recurrence (weeks) | Cause of Death |
|---|---|---|---|---|---|---|---|---|---|---|---|---|
| rM6 | NSCLC | 64 | F | Methylated | Wild Type | − | No | PD | — | 46 | 21 | Stroke |
| nM7 | SCLC | 61 | F | Methylated | Wild Type | + | Yes | CR | — | >40, alive | — | Alive |
| sL1 | PCNSL | 42 | M | ND | ND | + | Yes | CR/SD | — | >202, alive | — | Alive |
| nL2 | PCNSL | 51 | F | ND | ND | + | Yes | CR | — | >47, alive | — | Alive |
| nL3 | PCNSL | 75 | F | ND | ND | + | Yes | CR | — | 42 | — | Hospice |
| nPB1 | AA | 36 | F | ND | ND | − | Yes | CR | — | >78, alive | — | Alive |
| nPB2 | AA | 69 | M | Unmethylated | Wide Type | − | Yes | CR | — | >96, alive | — | Alive |
| rPB3 | AO | 55 | F | Methylated | Wild Type | − | No | SD | — | 113 | LTF | Hospice |
| rPB4 | GIII M | 63 | F | Methylated | Wild Type | + | Yes | CR | — | >170, alive | >50, alive | Alive |
| nGB1 | GB | 65 | M | Methylated | Wide Type | + | Yes | Near CR | — | 48 | — | Progressive Dementia |
| nGB2 | GB | 69 | M | ND | ND | + | Yes | PR | — | 34 | — | Progressive Dementia |
| rGB3 | GB | 38 | M | Ummethylated | Wide Type | + | Yes | PD | — | 256 | 29 | Tumor Progression |
| rGB4 | GB | 70 | F | Methylated | R132H | + | Yes | PR | Yes | 21 Years | 37 | Dementia |
| rGB5 | GB | 27 | F | Methylated | Wild Type | + | Yes | PR | Yes | >118, alive | >49, Alive | Alive |
| rGB6 | GB | 60 | F | Methylated | Wide Type | − | No | PD | — | 92 | 14 | Tumor Progression |
| rGB7 | GB | 53 | F | Methylated | Wild Type | − | No | PD | — | 71 | 35 | Tumor Progression |
| rGB8 | GB | 53 | F | Methylated | Wild Type | − | Yes | PR | — | 167 | 43 | Hospice |
| sGB9 | GB | 51 | M | ND | ND | − | Yes | CR/SD | — | 356 | 223 | H1N1 ARDS |
| rGB10 | GB | 63 | M | Unmethylated | Wide Type | − | Yes | PR | — | 95 | 90 | Alive |
| rGB11 | GB | 62 | M | Unmethylated | Wide Type | + | Yes | PD | — | 29 | 10 | Tumor Progression |
| nGB12 | GB | 53 | F | Equivocal | indeterminate | − | Yes | PR | — | >98, alive | — | Progressive Dementia |
| nGB13 | GB | 47 | M | Methylated | Wild Type | − | Yes | PR | — | 83 | — | Tumor Progression |
| rGB14 | GB | 49 | F | Unmethylated | Wide Type | − | No | PR | — | 42 | 30 | Tumor Progression |
| nGB15 | GB | 73 | M | Methylated | R132H | − | Yes | CR | — | 49 | — | Sudden Death |
| rGB16 | GB | 61 | M | Unmethylated | Wide Type | + | Yes | PD | — | 72 | 19 | Tumor Progression |
| nGB17 | GB | 56 | F | ND | ND | − | No | PD | — | 58 | — | LTF |
| rGB18 | GB | 51 | M | ND | ND | − | Yes | PD | — | 22 | 40 | LTF |
| nGB19 | GB | 57 | M | Unmethylated | Wide Type | − | Yes | PD | — | 28 | — | Tumor Progression |
| rGB20 | GB | 52 | F | ND | ND | − | No | PD | — | 17 | LTF | Tumor Progression |
| nGB21 | GB | 56 | M | Unmethylated | Wide Type | + | Yes | PR | — | >52, alive | — | Alive |
| nGB22 | GB | 47 | M | ND | ND | − | Yes | CR | — | >50, alive | — | Alive |

TABLE 2-continued

Clinical Summary of the 38 Subjects in the Immune Modulation Regimen Proof of Concept Study

| Case | Diagnosis | Diagnosis Age | Sex | MGMT | IDH1 | Cancerous Meningitis/ Ventriculitis | Immune Regimen | Response | Abscopal Effect | OS from Dx (weeks) | OS from Recurrence (weeks) | Cause of Death |
|---|---|---|---|---|---|---|---|---|---|---|---|---|
| nGB23 | GB | 67 | M | Methylated | Wild Type | − | Yes | CR | — | >47, alive | — | Alive |
| nGB24 | GB | 63 | M | Methylated | Wild Type | + | Yes | PR | — | 40 | — | Progressive Dementia |

GB: Glioblastomas;
DLBCL: Diffuse large B-cell lymphoma;
PCNSL: primary CNS lymphoma;
SCLC: Small Cell Lung Cancer;
NSCLC: Non-Small Cell Lung Cancer;
GE: Gastroesophageal cancer;
CUP: Cancer of unknown primary origin;
AA: Anaplastic Astrocytoma;
AO: anaplastic oligodendroglioma;
GIII M: anaplastic meningiomas;
PR: partial response;
CR: complete response;
PD: progressive disease;
SD: stable disease;
ND: not done;
LTF: Subjects Lost to Follow-up Subjects Table 2 lists the 7 metastatic (M) followed by the 3 primary CNS lymphoma (L) cases, the 4 other PB and the 24 GB subjects. The seven metastatic carcinoma cases include 6 subjects who took the immune modulating regimen and one who did not. For those taking the immune modulating regimen, 4 newly diagnosed (nM) each had a complete response; 1 subject with recurrent disease (rM1) had a near complete response and the other with progressive disease (rM5) had a partial response. The remaining subject (rM6) had multiple other medical issues in addition to recurrent lung cancer and chose not to take the immune modulating regimen. The 3 primary CNS lymphoma subjects all chose to take the immune modulating regimen, including 2 newly diagnosed (nL) subjects who had a complete response and the one with stable disease (sL) who remained in complete response. The 4 PB tumor subjects include 2 newly diagnosed (nPB) and 2 recurrent (rPB). The 3 who chose to take the immune modulating regimen had a complete response, whereas the remaining subject (rPB3) refused both the immune modulating regimen and additional therapy for recurrence. Of the 24 GB cases, 11 are newly diagnosed (nGB), 12 are recurrent (rGB), and 1 was a stable GB (sGB). Among the subjects with newly diagnosed GB, 10 of 11 chose to take the immune modulating regimen; all tumors responded, with 5 partial response, 3 complete response, 1 near complete response and one with progressive disease (PD). Importantly, the subject who took the immune modulating regimen but developed progression (nGB19) had multicentric GB with involvement of frontal and parietal lobes of both hemispheres and upper brainstem. A partial response was observed in all regions except the brainstem, which progressed and the subject refused additional treatment.

Eight of the 12 recurrent GB cases chose to take the immune modulating regimen. with 4 partial responses and 4 PD. Four of the 12 recurrent subjects with recurrent disease who did not take the immune modulating regimen had 3 PD (rGB6, rGB7 & rGB20) and 1 partial response (rGB14). The one stable case (sGB) had developed a recurrence at 2 years after his initial diagnosis with a subsequent complete response at 6 years post-diagnosis. One subject was initially placed on the immune modulating regimen, but chose not to take the flu vaccine due to concerns about vaccine-induced malaise and subsequently died from H1N1 ARDS at almost 7 years after initial diagnosis.

Surprisingly, when the components of the immune modulating regimen are combined, the regimen synergizes the effects of the individual components in reversing tumor-induced immunosuppression. Dying tumor cells from chemoradiation serve as antigenic templates to stimulate cell-mediated immune elimination of remaining intact tumor cells, presumably by fostering NK and CTL responses. An example of a putative immune response is the abscopal effect in which localized radiation results in regression of tumor mass(es) outside the radiation field. Spontaneous abscopal effects are rare, but have been reported in malignant melanoma, lymphoma, hepatocellular and renal cell carcinoma. Such abscopal effects can be enhanced by administration of immune therapies such as ipilimumab (Postow M A, et al. N Engl J Med 2012; 366(10): 925-31).

Six of 38 subjects exhibited unexpected abscopal effects, including a CNS melanoma subject who progressed on ipilimumab with radiotherapy. Eight subjects displayed robust radiologic responses and/or abscopal effects. Importantly, prolonged overall survival (OS) was also seen in these subjects with varied malignant primary tumors and metastatic cancers for which prognosis is generally measured in weeks from the time of diagnosis.

To investigate the impact of reversal of immunosuppression in cancer subjects, CSF cytokine profiles were assessed following the immune modulating regimen. Quantification of cytokines was performed using the Cytokine Human 30-Plex Panel for the Luminex® platform (Cat #LHC6003). Serum and CSF samples were undiluted. The multiplex immunoassay was performed as described by the manufacturer's protocol, using standards provided by the kit. Each sample was performed in duplicates. Each plate was read on the Luminex® 200™ system. Some samples were profiled 2~3 times to ensure assay reproducibility.

Figure 2:
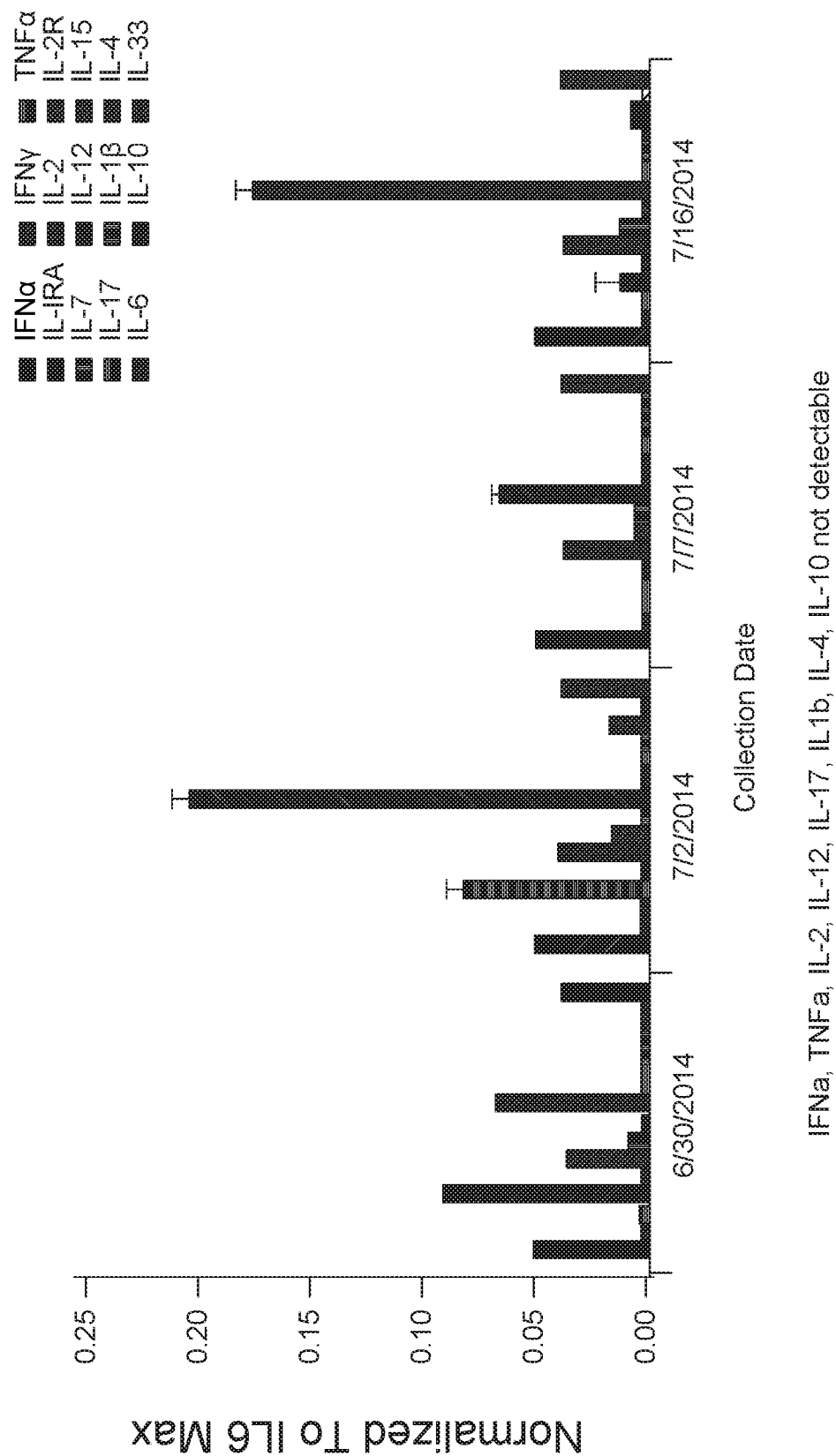
FIG. 2 is a graph showing the cytokine panel for a single subject receiving the immune modulating regimen comprising 7.5 mg Meloxicam, 120 mg caffeine, 40 mg famotidine, 280 mg of L-citrulline, 5,000 IU Vitamin A, 5,000 IU of Vitamin $D_3$.

The concentration of target cytokines in each sample was determined by interpolation from the standard curve incorporated into each assay. Experimental values outside the linear range of detection were discarded. Most CSF cytokines following the immune modulating regimen were unremarkable, with only IL-15 and IL-6 having consistent and measurable changes. CSF cytokines while on the immune modulating regimen revealed a pattern of increased IL-15 levels, and CSF ratio of IL-15/IL-6 expression and/or activitys were consistently >1, correlating with the striking clinical and radiological responses the subjects displaying an inflammatory response. This response was a specific response, and demonstrated an isolated immune response when examining a panel of cytokines. See FIG. 2, which shows the cytokine response for a panel of 15 cytokines in a single subject, subject M1, following administration of the immune modulating regimen as described below.

The values obtained from separate experiments were normalized to the maximal IL-6 level in each assay, which removed variability among experimental sets. For samples with undetectable IL-6, the IL-6 level was considered to be zero. The IL-15 level is presented individually and as an ratio of IL-15/IL-6 expression and/or activity. When IL-6 was not detectable, the ratio was assigned an infinite numeric value and labeled as "inf". Results are shown in FIGS. 3-5.

Figure 3:
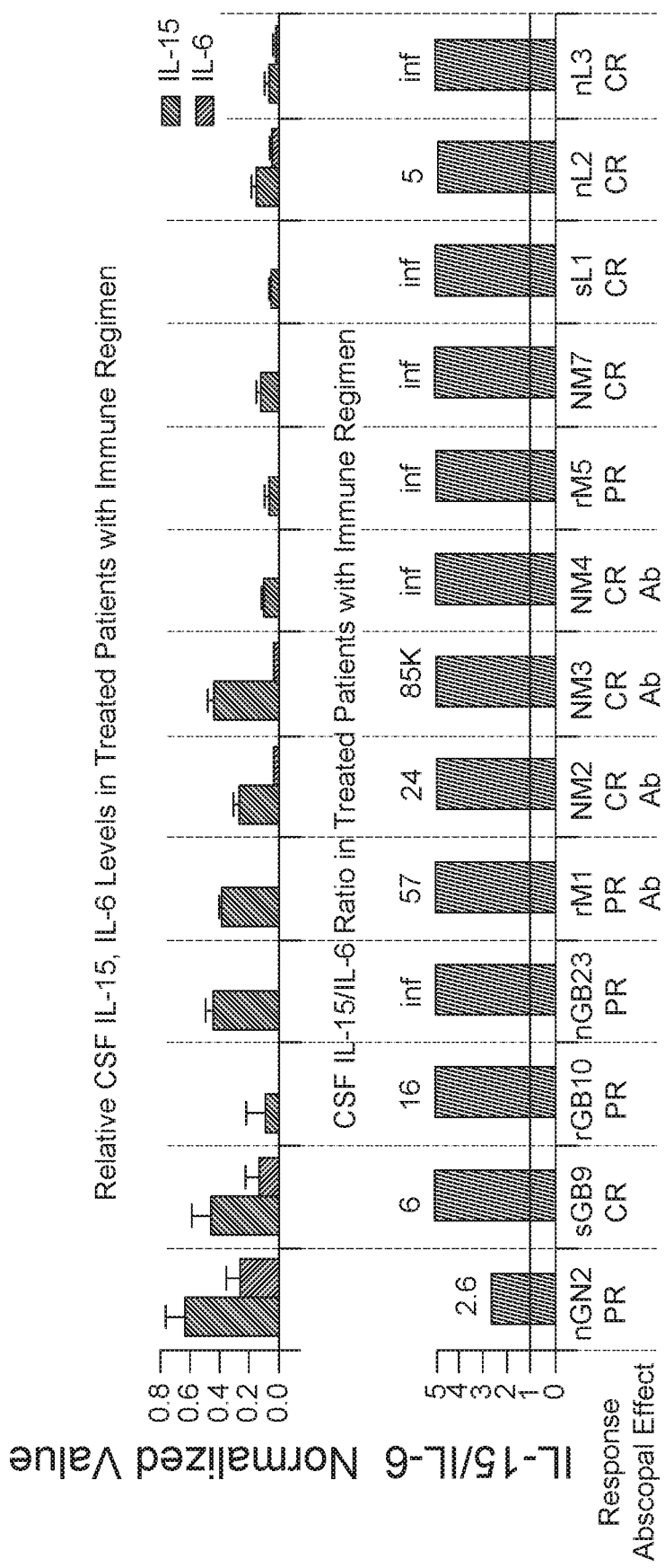
FIG. 3 is a diagram illustrating the relative CSF IL-15 and IL-6 levels and ratios in subjects with various cancers treated with the immune modulating regimen comprising 7.5 mg Meloxicam, 120 mg caffeine, 40 mg famotidine, 280 mg of L-citrulline, 5,000 IU Vitamin A, 5,000 IU of Vitamin $D_3$.

FIG. 3 shows the overall levels of IL-15 and IL-6 and the ratio of IL-15/IL-6 expression and/or activity in the CSF samples of each of the subjects following the immune modulating regimen. CSF of responders treated with CRT and the immune modulating regimen achieved a partial response, complete response and/or abscopal effects. Their CSF ratio of IL-15/IL-6 expression and/or activitys were uniformly >1. Most GB subjects responded with a partial response, whereas most subjects with metastatic cancer and primary CNS lymphoma had a complete response, some exhibiting abscopal effects.

Figure 4:
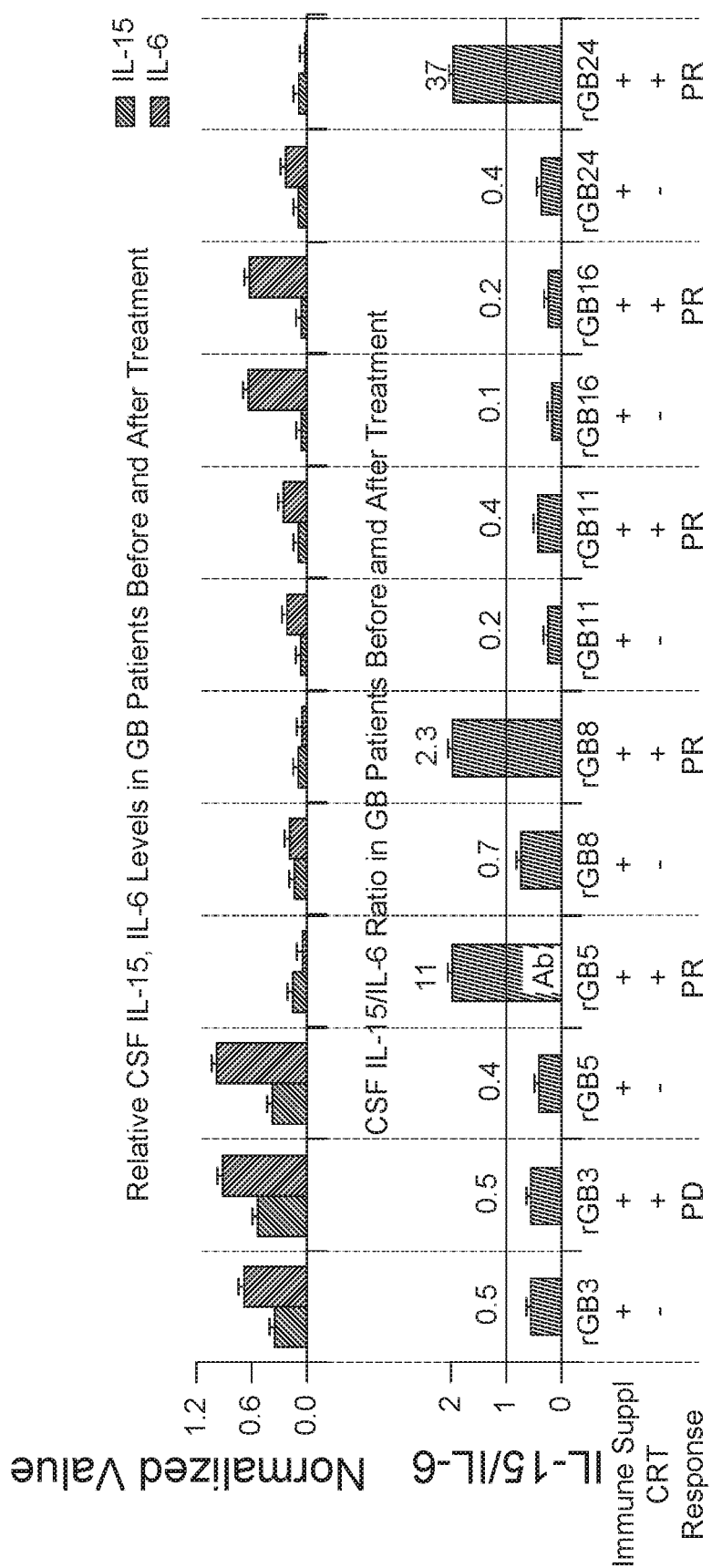
FIG. 4 is a diagram illustrating the relative CSF IL-15 and IL-6 levels and ratios in subjects with glioblastoma treated with the immune modulating regimen comprising 7.5 mg Meloxicam, 120 mg caffeine, 40 mg famotidine, 280 mg of L-citrulline, 5,000 IU Vitamin A, 5,000 IU of Vitamin $D_3$.

FIG. 4 shows the overall levels of IL-15 and IL-6 and the ratio of IL-15/IL-6 expression and/or activity in the CSF samples in a subset (glioblastoma subjects) of the subjects following the immune modulating regimen before and after first-line or rescue chemoradiotherapy. At diagnosis or recurrence, ratio of IL-15/IL-6 expression and/or activitys were consistently <1 in 6 GB subjects. Responding GB subjects (rGB5, rGB8 and nGB24) had post-therapy ratios that increased to >1, whereas nonresponders (rGB3, rGB11, and rGB16) had ratio of IL-15/IL-6 expression and/or activitys that remained <1.

Figure 5:
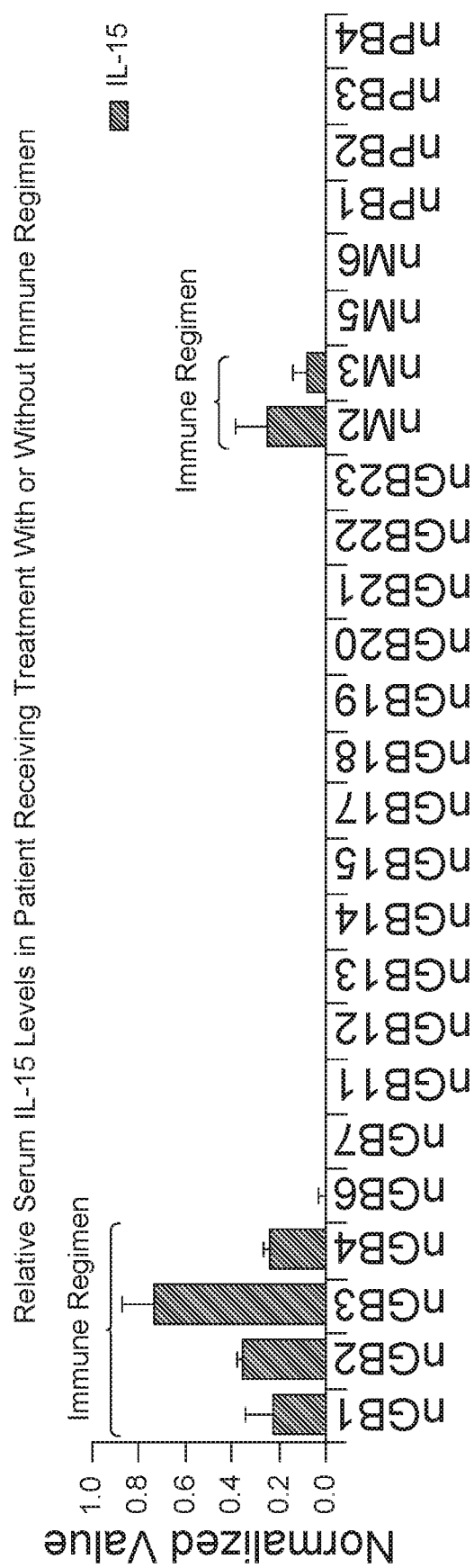
FIG. 5 is a diagram illustrating relative serum IL-15 levels in subjects receiving treatment for malignancy either with or without the immune modulating regimen comprising 7.5 mg Meloxicam, 120 mg caffeine, 40 mg famotidine, 280 mg of L-citrulline, 5,000 IU Vitamin A, 5,000 IU of Vitamin $D_3$.

FIG. 5 is the overall IL-15 levels in subjects that did or did not receive the immune modulating regimen. Twenty samples were taken from subjects presenting with newly diagnosed (n) or recurrent (r) GB, carcinoma with CNS metastases, and other primary brain tumors before offering the immune modulating regimen. These levels were very low or undetectable. In contrast, all 6 serum samples obtained from individuals while taking the immune modulating regimen had significantly higher levels of IL-15.

The observed clinical and radiological responses translated into prolonged survival (table 1), versus an OS of mere weeks from diagnosis. For example, the prognosis of carcinomatous meningitis is poor, with a median survival from diagnosis of 6-9 weeks (Gleissner B and Chamberlain M C. *Lancet Neurol* (2006) 5(5): 443-52.) However, four subjects with carcinomatous meningitis (M1-M4) had an OS of 6 to 12+ months during treatment with the immune modulating regimen plus CRT. Two of the four, 74- and 79-year old subjects, died without evidence of tumor recurrence at 6 months and 12 months, respectively, from diagnosis. The other two are doing well on maintenance therapy.

Serum and CSF IL-15 levels increased in all subjects receiving the immune modulating regimen with the CSF ratio of IL-15/IL-6 expression and/or activitys correlating with radiological response. Newly diagnosed and recurrent GB subjects had a CSF ratio of IL-15/IL-6 expression and/or activity <1. All responding GB and metastatic carcinoma subjects had a CSF ratio of IL-15/IL-6 expression and/or activity >1, including a melanoma subject who had previously progressed on ipilimumab. In contrast, the CSF ratio of IL-15/IL-6 expression and/or activity of nonresponding GB cases remained below 1. In summary, an ratio of IL-15/IL-6 expression and/or activity >1 was detected only in responding subjects versus <1 in subjects with disease progression or nonresponding subjects, suggesting that this ratio can be used as a marker of treatment response. The ability of the immune modulating regimen to reverse tumor-mediated immunodeficiency in the CNS raises the possibility that it could also be successful in reversing tumor-mediated immunosuppression in the microenvironment of solid tumors throughout the body.

In summary, impressive clinical and radiological responses were observed in subjects receiving the immune modulating regimen coupled with standard therapy, including eight unprecedented responses versus otherwise historically devastating clinical outcome. Typically unresponsive to standard chemoradiotherapy, the CSF-involved portion of the malignancy demonstrated superior regression compared with parenchymal cancer in the same subjects. Additionally, six subjects exhibited unexpected abscopal effects, including a CNS melanoma subject who progressed on ipilimumab. Cytokine analyses in CSF and sera from these subjects revealed elevated IL-15. Responders consistently had a CSF ratio of IL-15/IL-6 expression and/or activity above 1 contrasted with nonresponders who had a ratio below 1.

Example 2: Robust Responses from a Cohort of Subjects with Metastatic Carcinoma Using Chemoradiation Plus the Immune Modulating Regimen Four different metastatic carcinoma cases, M1-M4, demonstrated abscopal effects when the immune modulating regimen was combined with standard chemoradiotherapy. A summary of the metastatic carcinoma subjects and their outcomes is summarized in Table 3:

TABLE 3

Clinical Summary of 4 Subjects with Metastatic Carcinoma Following the Immune Modulation Regimen

| Case | Diagnosis | Age of Dx | Sex | Immune regimen | Location | CNS Response | Systemic Response | Abscopal Effect | OS from Dx (weeks) | OS from Recurrence (weeks) | Cause of Death |
|---|---|---|---|---|---|---|---|---|---|---|---|
| M1 | Melanoma | 53 | F | Yes | Leptomeninges of brain and spine, T9 intramedullary thoracic spine | PR | NA | Yes | >56, alive | >36 | Alive |

TABLE 3-continued

Clinical Summary of 4 Subjects with Metastatic Carcinoma Following the Immune Modulation Regimen

| Case | Diagnosis | Age of Dx | Sex | Immune regimen | Location | CNS Response | Systemic Response | Abscopal Effect | OS from Dx (weeks) | OS from Recurrence (weeks) | Cause of Death |
|---|---|---|---|---|---|---|---|---|---|---|---|
| M2 | CUP | 72 | F | Yes | Nerve roots of the cauda equina, conus, ventricle, cerebellum, vermis equina and the surface of the conus medullaris | CR | NA | Yes | 34 | NA | CHF |
| M3 | NSCLC | 79 | F | Yes | Temporal lobe, cerebellum, vermis | CR | CR | Yes | 51 | NA | VPS failure |
| M4 | GE | 60 | M | Yes | Left inferior cerebellum, right orbit and anterior temporalis muscle | CR | CR | Yes | >36, alive | NA | Alive |

The first subject, M1, was a 53-year-old female who had developed progressive metastatic melanoma with rapid cognitive decline. She was diagnosed with a T9 intramedullary enhancing melanoma that was treated with radiation to T8-T10 (10 fractions plus 2 boosts for a total of 36Gy) followed by 4 cycles of ipilimumab. Magnetic resonance imaging (MRI) at 4.5 months after diagnosis showed progressive enhancements along the leptomeninges of her spinal cord and brain. The subject was initiated on the immune modulating regimen with whole brain radiation (WBRT) and intrathecal (IT) therapy with cytarabine (Ara-C). MRI 6 months after progression (10.5 months from diagnosis) demonstrated significantly decreased enhancement with a near complete response in the brain with abscopal effects of a complete response of lower thoracic enhancing nodules and a partial response of spinal leptomeningeal enhancement, which did not receive additional radiation. This subject was still alive 1 year after diagnosis, considerably longer than the median survival time of 10 weeks for melanoma with cancerous meningitis (Harstad L et al. *Neuro Oncol* 2008; 10(6): 1010-8).

The second subject, M2, was a 74-year-old female who had prior chemotherapy for T-cell lymphoma and presented with gait difficulty and leg weakness. MRI showed nodular enhancement along the cauda equina nerve roots, lateral ventricle, interpeduncular cistern and cerebellum. CSF cytology was consistent with carcinoma of unknown primary (CUP) with no systemic disease. Radiation to the lumbosacral region was initiated along with the immune modulating regimen administration. However, due to marked pancytopenia, radiotherapy was discontinued after only 9Gy (or 3 fractions) of the planned 30Gy. The subject tolerated IT methotrexate/cytarabine (MTX-Ara-C) given every 2-4 weeks. MRI 6 months after the CUP diagnosis showed a complete response of nodular lumbosacral enhancement and enhancements in the brain, which had received no radiation. There was no evidence of recurrence before her death from progressive congestive heart failure.

The third subject, M3 was a 79-year-old female was diagnosed with non-small cell lung cancer (NSCLC) and brain metastases. The immune modulating regimen was initiated after resection of the largest metastasis of the posterior fossa. Due to the subject's cognitive impairment, WBRT was avoided. Thus, at 3 weeks after diagnosis she had a single fraction of 21Gy radiosurgery to the frontal lesion (not shown) and the two cerebellar lesions. A ventriculoperitoneal shunt (VPS) was placed for communicating obstructive hydrocephalus. An MRI immediately before scheduled radiosurgery showed two additional enhancing lesions, which were not included in the treatment plan. One month after radiosurgery, all enhancing lesions, including 2 nonradiated masses and post-surgical cavity, had a complete response before initiation of systemic chemotherapy. Additionally, complete response of lung disease was found after only 2 of 6 planned cycles of systemic chemotherapy. The cognitive impairment resolved after VPS placement, however, after one year complications developed related to the VPS, with no radiographic evidence of tumor recurrence, and she was referred to local hospice.

The fourth subject, M4, was a 60-year-old man with metastatic gastroesophageal (GE) carcinoma initiated the immune modulating regimen after a subtotal resection of a mass encompassing the right periorbital region and temporal muscle, causing right eye proptosis. Radiosurgery was delivered to a discrete cerebellar enhancing mass while waiting for the periorbital region to heal. Follow-up imaging showed complete response of residual enhancement in the nonradiated periorbital postoperative site (and radiated cerebellar mass) before systemic chemotherapy was initiated, representing an abscopal effect (images not shown). Positron emission tomography (PET) subsequent to standard systemic chemotherapy showed complete response of the GE primary mass as well as the extensive metastatic involvement of lymph nodes, liver and bone. The subject is doing well 9 months after diagnosis.

Figure 6:
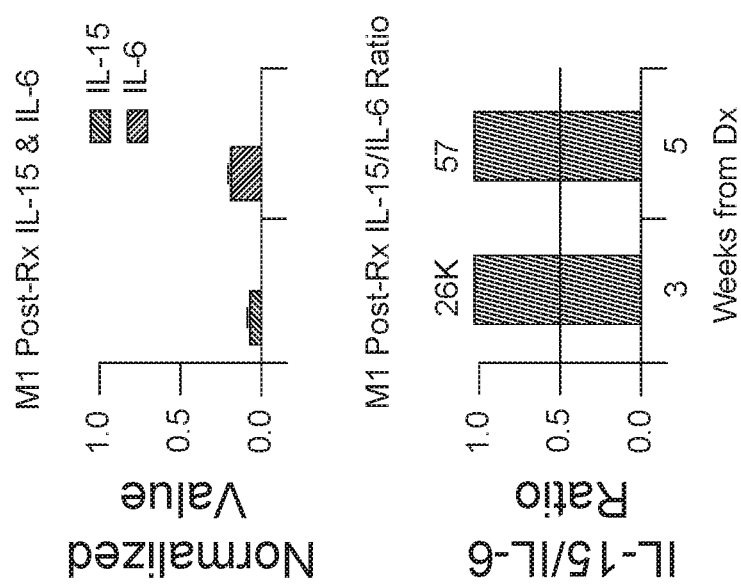
FIG. 6 is a diagram illustrating the CSF IL-15/IL-6 levels and ratios in a first subject with metastatic carcinoma six months following the immune modulating regimen comprising 7.5 mg Meloxicam, 120 mg caffeine, 40 mg famotidine, 280 mg of L-citrulline, 5,000 IU Vitamin A, 5,000 IU of Vitamin $D_3$.
Figure 7:
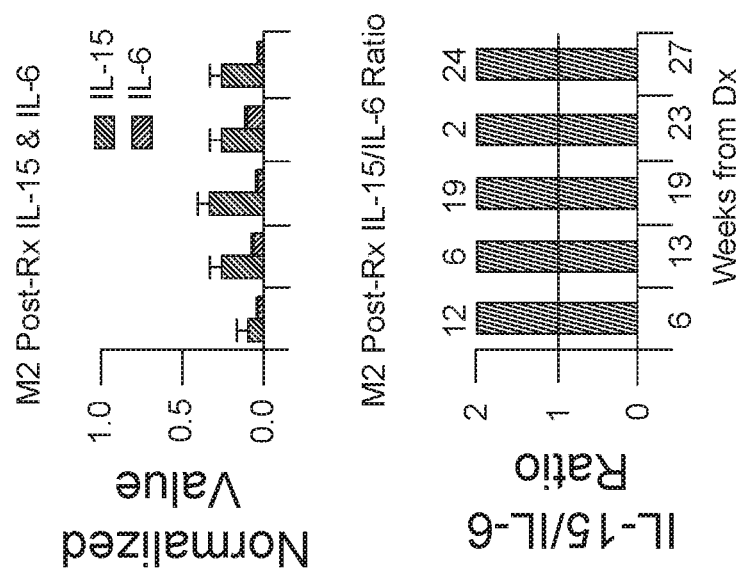
FIG. 7 is a diagram illustrating the CSF IL-15/IL-6 levels and ratios in a second subject with metastatic carcinoma six months following the immune modulating regimen comprising 7.5 mg Meloxicam, 120 mg caffeine, 40 mg famotidine, 280 mg of L-citrulline, 5,000 IU Vitamin A, 5,000 IU of Vitamin $D_3$.
Figure 8:
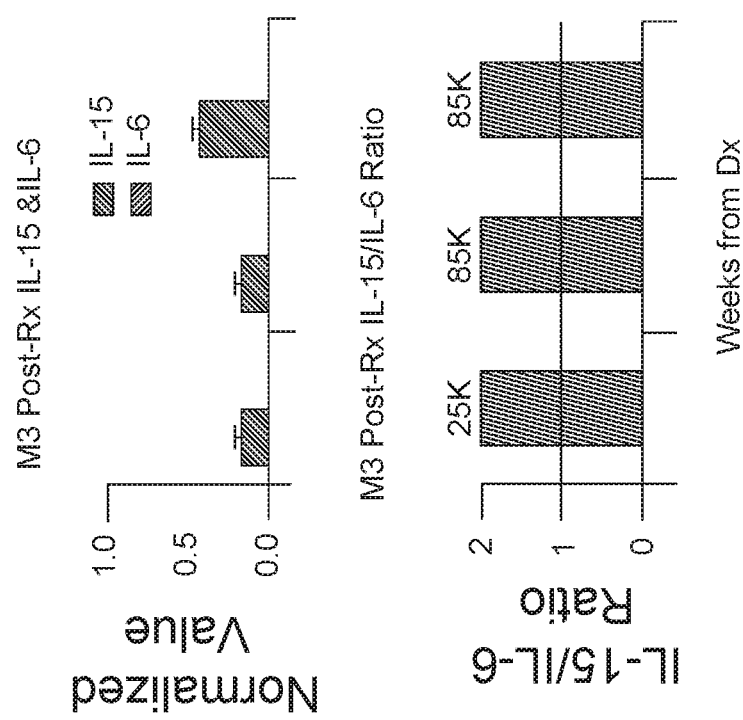
FIG. 8 is a diagram illustrating the CSF IL-15/IL-6 levels and ratios in a third subject with metastatic carcinoma six months following the immune modulating regimen comprising 7.5 mg Meloxicam, 120 mg caffeine, 40 mg famotidine, 280 mg of L-citrulline, 5,000 IU Vitamin A, 5,000 IU of Vitamin $D_3$.

Impressive clinical and radiological responses were observed in each of these subjects following the immune modulating regimen coupled with therapy. Each of the subjects displayed both an increased level of IL-15 and an increased ratio of IL-15/IL-6 expression and/or activity. These values are shown for subjects M1, M2 and M3 in FIGS. 6-8, respectively. Each subject showed a ratio of IL-15/IL-6 expression and/or activity greater than 1, consistent with the findings from the larger cohort.

Example 3: Robust Responses from a Cohort of Glioblastoma (GB) Subjects Using Chemoradiation with Chemoradiation Plus the Immune Modulation Regimen Butterfly GB represents the most aggressive form of GB and has the worst prognosis, with an estimated survival of approximately 48 days in 12 subjects who received CRT but could not have their tumors resected (Stupp R et al. *N Engl J Med* (2005) 352(10): 987-96). Three unresectable subjects with butterfly GB who were treated with the immune modulating regimen as well as standard CRT. A summary of the GB subjects and their outcomes as of Feb. 20, 2015 is summarized in Table 4:

TABLE 4

Clinical Summary of 5 Subjects with Glioblastoma Following the Immune Modulation Regimen

| Case | Diagnosis | Age at Dx | Sex | Location | MGMT | IDH1 | Response | Abscopal Effect | OS from Dx (weeks) | OS from Recurrence (weeks) | Cause of Death |
|---|---|---|---|---|---|---|---|---|---|---|---|
| GB1 | Butterfly GBM | 65 | M | Right frontal lobe, bi-parietal lobe, splenium of corpus, callosum (CC), lateral verticles | Methylated | Wild Type | Near CR | NA | 48 | NA | Progressive Dementia* |
| GB2 | Butterfly GBM | 69 | M | Bi-frontal and bi-parietal lobes, splenium of CC | ND | ND | PR | NA | 34 | NA | Progressive Dementia* |
| GB3 | Butterfly GBM | 38 | M | Right parieto-occipital lobe, the posterior horn of the lateral verticles, splenium of CC | Unmethylated | Wild Type | PD | NA | 256 | 29 | Tumor Progression |
| GB4 | GBM | 70 | F | Left temporofrontal, right verticle and basal cistern | Methylated | R132H | PR | Yes | 21 Years | 37 | Progressive Dementia* |
| GB5 | GBM | 27 | F | Bi-frontal lobes, inferior colliculi, left cerebellum & vermis, T6, cervical, thoracic lumbar spine | Unmethylated | Wild Type | PR | Yes | >118 | >49, Alive | Alive |

The first two GB subjects, GB1 and GB2, were 65- and 69-year-old men, respectively, with newly diagnosed butterfly GB involving the splenium of the corpus callosum. Both were given the immune modulating regimen with standard CRT (intensity-modulated radiation therapy [IMRT] and oral temozolomide (Stupp R et al., *N Engl J Med* (2005) 352(10): 987-96). At 7 months, MRI revealed near total regression of tumor in GB1 and partial regression in GB2. Of particular note, the ventricular component of the glioma responded more readily than did the intraparenchymal mass in both of these cases.

Figure 10:
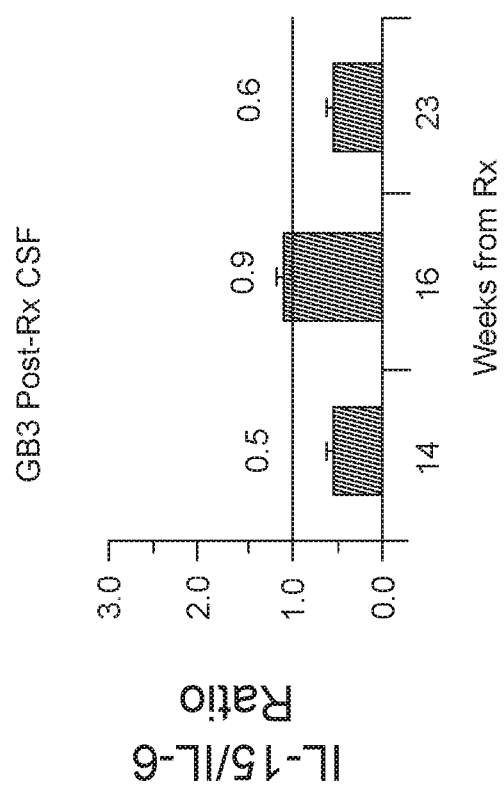
FIG. 10 is a diagram illustrating the CSF ratio of IL-15/IL-6 expression and/or activity in a second subject with glioblastoma seven months following the immune modulating regimen comprising 7.5 mg Meloxicam, 120 mg caffeine, 40 mg famotidine, 280 mg of L-citrulline, 5,000 IU Vitamin A, 5,000 IU of Vitamin $D_3$.

The third subject, GB3, was a 40-year-old man with prior IMRT/temozolomide therapy to a left temporal lobe GB and 2 years of standard oral temozolomide (200 mg/m$^2$ daily 5/28 days). GB3 developed recurrent GB involving the splenium of the corpus callosum at 4 years after initial diagnosis. He was treated with IMRT, temozolomide and IT MTX/Ara-C in addition to the immune modulating regimen but did not respond clinically or radiologically (FIG. 10).

Figure 9:
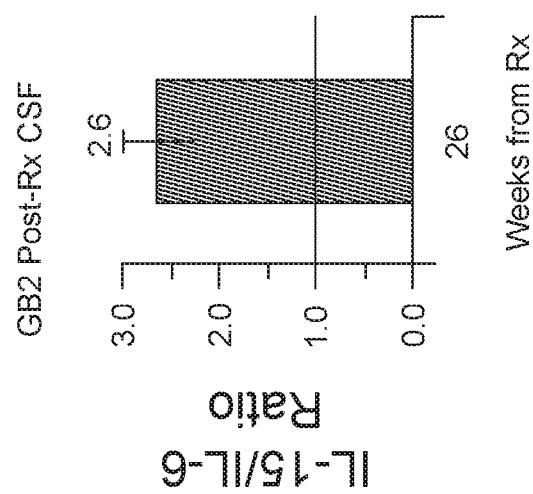
FIG. 9 is a diagram illustrating the CSF ratio of IL-15/IL-6 expression and/or activity in a first subject with glioblastoma seven months following the immune modulating regimen comprising 7.5 mg Meloxicam, 120 mg caffeine, 40 mg famotidine, 280 mg of L-citrulline, 5,000 IU Vitamin A, 5,000 IU of Vitamin $D_3$.

Despite the lack of radiologic regression in GB3, all three subjects, GB1, GB2 and GB3 had an OS of 7 to 11 months, which is markedly longer than expected versus historical controls with an estimated survival of approximately 48 days (Dziurzynski K et al. *J Neurooncol* (2012) 109(3): 555-63. Similar to responding subjects with metastatic disease, CSF from responding GB2 obtained at 26 weeks showed an ratio of IL-15/IL-6 expression and/or activity that was >1 (FIG. 9). In contrast, the nonresponder (GB3), who had 3 CSF samples analyzed, maintained CSF ratio of IL-15/IL-6 expression and/or activitys <1 (FIG. 10).

Example 4: Abscopal Effects in GB with Chemoradiation Plus Immune Modulation Therapy In two additional subjects, GB4 and GB5, unexpected abscopal effects were observed following the immune modulating regimen. GB4 was a 70-year-old female who presented with a left temporofrontal GB after receiving radiation to a left temporal ganglioglioma 21 years earlier. She was treated with temozolomide and the immune modulating regimen. Radiotherapy was initiated at 3.5 months for radiographic progression, which was interrupted after only 5 fractions of 1.8Gy due to emergent abdominal surgery. Abscopal effects were seen in the tumors outside the radiotherapy treatment field with complete response of tumors at 1 month after receiving only 9Gy of the planned 30Gy. She subsequently succumbed to complications related to progressive cumulative treatment-related dementia and her family requested hospice care.

Figure 11:
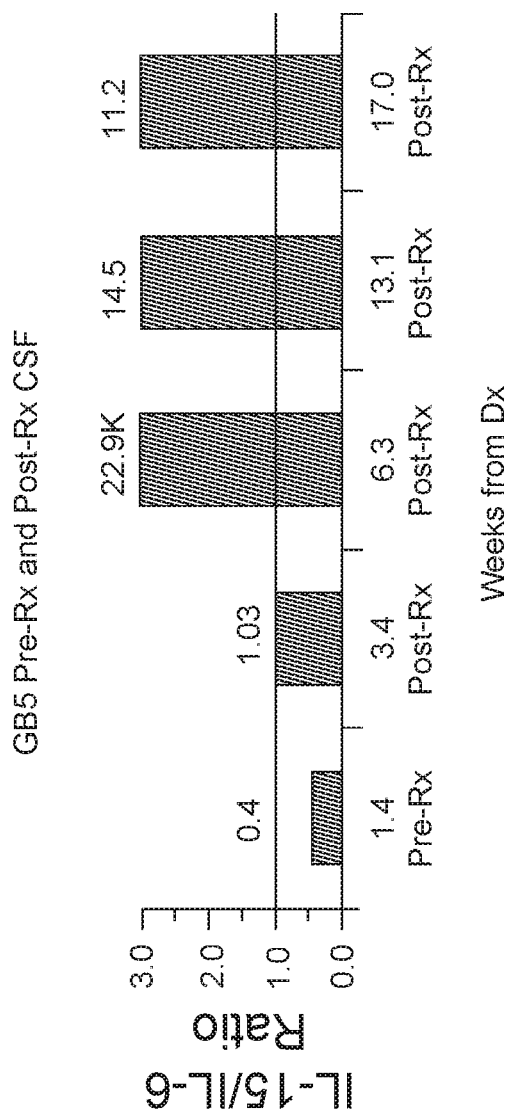
FIG. 11 is a diagram illustrating the CSF ratio of IL-15/IL-6 expression and/or activity in a third subject with glioblastoma seven months following the immune modulating regimen comprising 7.5 mg Meloxicam, 120 mg caffeine, 40 mg famotidine, 280 mg of L-citrulline, 5,000 IU Vitamin A, 5,000 IU of Vitamin $D_3$.

GB5 was a 27-year-old female with a bifrontal GB previously treated with standard IMRT plus temozolomide and 16 months of maintenance temozolomide when presenting with numbness in the left chest and both legs. An MRI showed tumor progression involving inferior colliculi and cerebellum, intramedullary T6 spinal mass, and extensive leptomeningeal involvement along her entire spinal cord. She received 30Gy of fractionated radiation between T3 and S1, and gamma knife (13Gy) to the inferior colliculi. After radiation, she also received IT MTX-Ara-C with oral cyclophosphamide (75 mg/m$^2$ daily for 21/28 days) and thalidomide (200 mg nightly) in combination with the immune modulating regimen. MRI at 7 months after recurrence showed partial response in the radiated inferior colliculi, T6 intramedullary mass and enhancements along T3 to S1 region of the spinal cord. Furthermore, complete response was noted in 3 nonradiated cerebellar lesions and a partial response in nonradiated enhancements around the cervical and upper thoracic spine. Consistent with our other observations, at recurrence the CSF had an ratio of IL-15/IL-6 expression and/or activity <1 but after treatment with additional CRT plus the immune modulating regimen, her four CSF ratio of IL-15/IL-6 expression and/or activitys were consistently >1 (FIG. 11). She remains on maintenance therapy 11 months from progression with near complete response.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. All references cited herein are incorporated by their entirety for all purposes.

The invention claimed is:

1. A composition comprising a pharmaceutically acceptable dosage of famotidine, caffeine, meloxicam, vitamin A, cholecalciferol, and citrulline.

2. The composition of claim 1, wherein the composition comprises about 40 mg of the famotidine.

3. The composition of claim 1, wherein the composition comprises from about 100 to about 200 mg of caffeine.

4. The composition of claim 1, wherein the composition comprises about 7 mg of Meloxicam.

5. The composition of claim 1, wherein the composition comprises about 5,000 IU of cholecalciferol.

6. The composition of claim 1, wherein the composition comprises about 5,000 IU of vitamin A.

7. The composition of claim 1, wherein the composition comprises 7.5 mg Meloxicam, 120 mg caffeine, 40 mg famotidine, 280 mg of L-citrulline, 5,000 IU Vitamin A, and 5,000 IU of Vitamin $D_3$.

8. A method of increasing the ratio of interleukin-15/interleukin-6 in a subject with a malignancy comprising administering to said subject a composition of claim 1.

9. The method of claim 8, wherein the malignancy is glioblastoma multiforme.

* * * * *